(12) United States Patent
Park et al.

(10) Patent No.: US 8,060,217 B2
(45) Date of Patent: Nov. 15, 2011

(54) NEURAL DEVICE USING AT LEAST ONE NANO-WIRE

(75) Inventors: Seung Han Park, Seoul (KR); Jong Il Hong, Seoul (KR); Jae Young Choi, Seoul (KR); Heon Jin Choi, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 12/301,790

(22) PCT Filed: Feb. 18, 2008

(86) PCT No.: PCT/KR2008/000933
§ 371 (c)(1),
(2), (4) Date: Feb. 17, 2010

(87) PCT Pub. No.: WO2009/054575
PCT Pub. Date: Apr. 30, 2009

(65) Prior Publication Data
US 2010/0305657 A1    Dec. 2, 2010

(30) Foreign Application Priority Data
Oct. 23, 2007    (KR) .................. 10-2007-0106752

(51) Int. Cl.
*A61N 1/05* (2006.01)
(52) U.S. Cl. .................. 607/115; 607/45; 607/117
(58) Field of Classification Search .............. 607/45, 607/115–117, 137; 600/377–379
See application file for complete search history.

(56) References Cited

U.S. PATENT DOCUMENTS

| 7,006,859 | B1 * | 2/2006 | Osorio et al. ............. 600/378 |
| 2007/0187238 | A1 * | 8/2007 | Whalen et al. ............ 204/400 |
| 2008/0161887 | A1 * | 7/2008 | Hagen ....................... 607/72 |

OTHER PUBLICATIONS

Wang et al. "Fabrication of a carbon nanotube protruding electrode array for retinal prosthesis"; Microfluids, BioMEMS, and Medical Microsystems III, Proceedings of SPIE vol. 5718 (SPIE, Bellingham WA, 2005).*
Llinas et al.; "Neuro-vascular central nervous recording/stimulating system: Using Nanotechnology Probes"; Journal of Nanoparticle Research (2005) 7:111-127.*
Office Action dated Oct. 19, 2009, issued in South Korean Patent Application No. 10-2008-0086410.

* cited by examiner

*Primary Examiner* — Carl H Layno
*Assistant Examiner* — Paula J Stice
(74) *Attorney, Agent, or Firm* — Holme Roberts & Owen LLP

(57) ABSTRACT

The present invention relates to a neural device comprising wires transmitting and receiving electric signals. More specifically, the present invention relates to a structure of the neural device comprising wires which effectively obtain electric signals developed in nerve fibers and transmit electric stimuli to the nerve fibers.

The neural device according to the present invention is connected to a processing module processing electric signals detected from nerve fibers, and the neural device is inserted in nerve fibers via nanowires to obtain electric signals from the nerve fibers, or inserted in the nerve fibers to transmit electric stimuli. The neural device may further provide with at least one through-hole and support.

The neural device according to the present invention has an advantage that may obtain electric signals without killing nerve fibers or provide them with electric stimuli.

7 Claims, 8 Drawing Sheets

NEURAL DEVICE USING AT LEAST ONE NANO-WIRE

CROSS REFERENCE TO RELATED APPLICATIONS

This application is a national stage application under 35 U.S.C. 371 of PCT Application No. PCT/KR2008/000933 having an international filing date of 18 Feb. 2008, which designated the United States, which PCT application claimed the benefit of Korea Application No. 10-2007-0106752 filed 23 Oct. 2007, the entire disclosure of each of which are hereby incorporated herein by reference.

TECHNICAL FIELD

The present invention relates to a neural device comprising wires transmitting and receiving electric signals. More specifically, the present invention relates to a structure of the neural device comprising wires which effectively obtain electric signals developed in nerve fibers and transmit electric stimuli to said nerve fibers.

BACKGROUND ART

Conventional devices are described as follows, which detect electric signals developed in human body.

Figure 1:
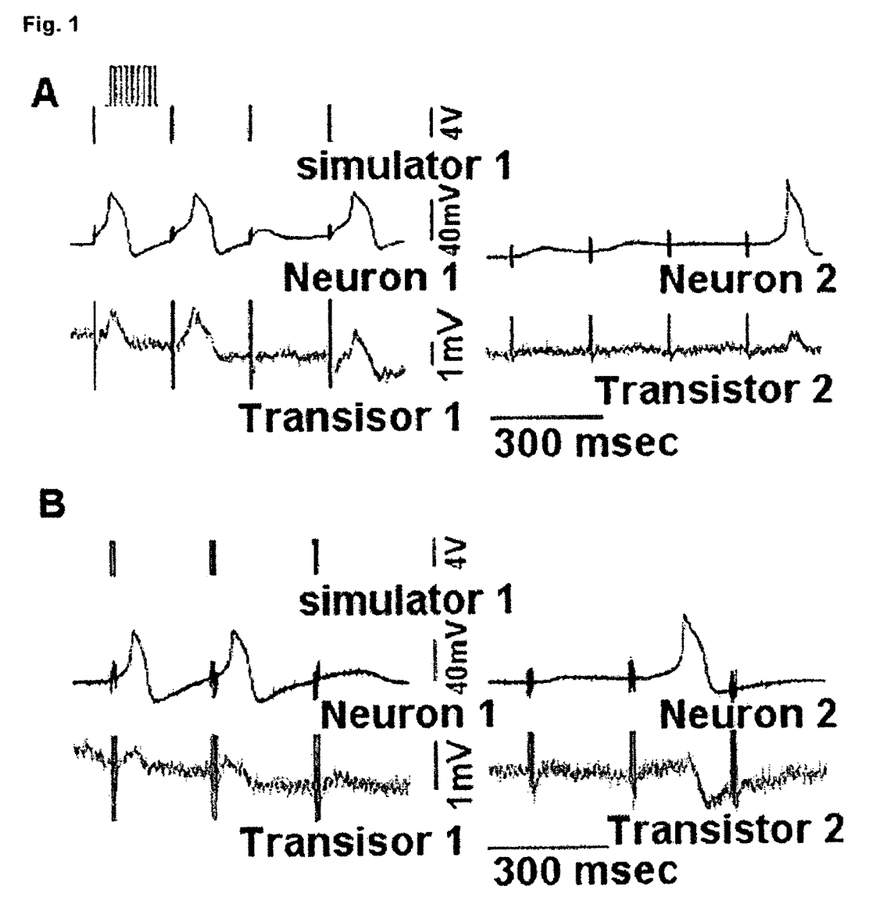
FIG. 1 represents intra-cellular signals and extra-cellular signals detected according to the first prior art.

First, a device detecting electric signals of nerves, based on MOSFET (Metal-Oxide-Semiconductor Field Effect Transistor), was conventionally proposed. This prior art is a technique monitoring change of membrane capacitance depending on exterior stimuli by using gatings of MOSFET device, moreover a technique simultaneously monitoring various neural responses. This prior art has been applied to a method of detecting nerve signals by fixing positions of snail neurons around P-MOSPET with picket fences made of polyimide and culturing them with limiting mobility (Zeck et. al., Non-invasive neuroelectronic interfacing with synaptically connected snail neurons immobilized on a semiconductor chip, Proc Nat Acad Sci 2001; 98). FIG. 1 is represents intra-cellular signals and extra-cellular signals detected according to such first prior art.

Figure 2:
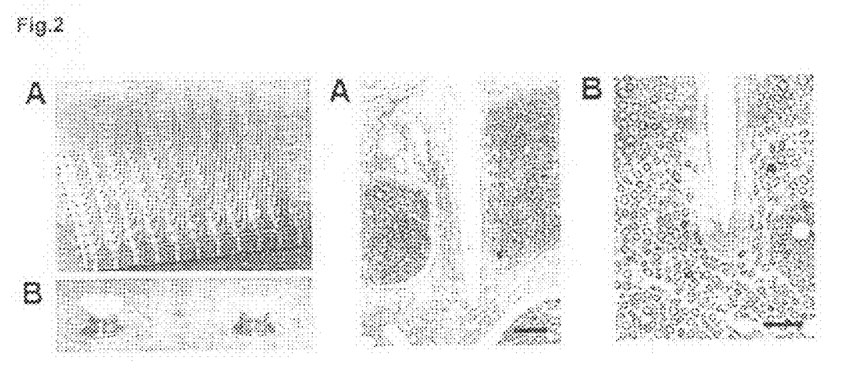
FIG. 2 represents multi-electrodes according to the second prior art and a shape that these electrodes are inserted in cat sciatic nerve.

Second, a technique for detecting electric stimuli of brain stems or nerve fibers was proposed. Normann group of University of Utah (USA) and Cyberkinetics have been proceeding a research to measure electric signals and stimulate nerves by directly inserting multi-electrodes in nerves and brains since 2000 (Normann et. al., Long-Term Stimulation and Recording With a Penetrating Microelectrode Array in Cat Sciatic Nerve, IEEE Transactions on Biomedical Engineering, VOL. 51, NO. 1, JANUARY 2004). FIG. 2 represents multi-electrodes according to the second prior art and a shape that these electrodes are inserted in cat sciatic nerve.

Figure 3:
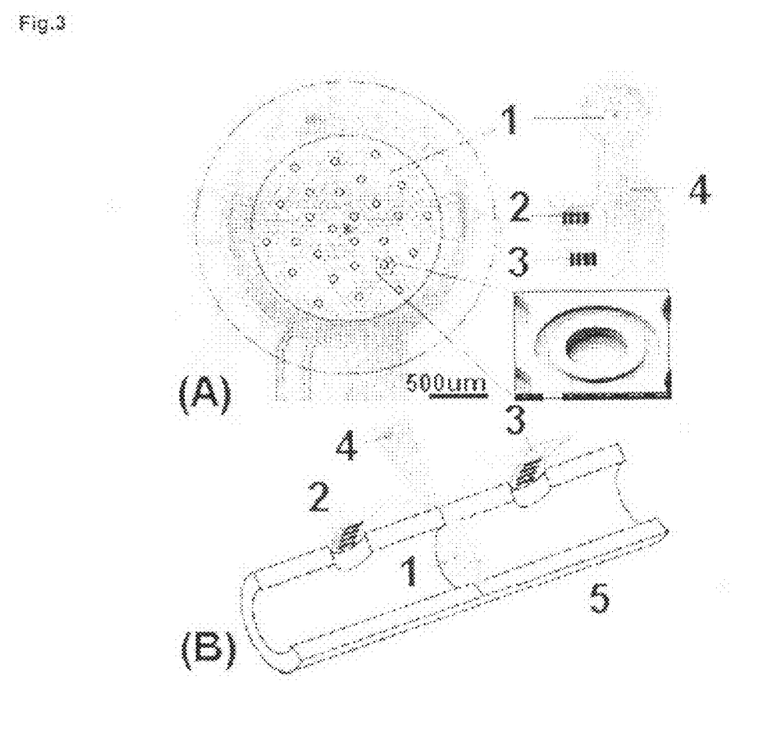
FIG. 3 represents sieve electrodes based on the third prior art.

Third, a technique inserting sieve electrodes in nerve fibers was proposed. Through joint researches of Fraunhofer-IBMT (Germany), IMTEK (Germany) and the like, regeneration of nerve has been studied and recording of nerve signals is attempted, by inserting sieve electrodes to be curved, in nerve fibers and transmitting electric stimuli thereto (Anup et. al., Design, in vitro and in vivo assessment of a multi-channel sieve electrode with integrated multiplexer, J. Neural Eng. 3 (2006) 114-24). FIG. 3 represents the sieve electrodes based on the third prior art as described above. Total diameter of the sieve is the same as that of rat sciatic nerve (1.5 mm), and 571 holes having a diameter of 40 µm are disposed therein at 70 µm intervals. In addition, electrodes of ring shape cover 27 holes and their area is 2200 µm².

DISCLOSURE

Technical Problem

In case of the prior art of FIG. 1 as described above, there is a problem that noise of the MOSFET device is high and thus only a tendency of electric signals can be measured.

Further, in case of the prior art of FIG. 2 as described above, there is a problem that on inserting electrodes, cells such as brain stems or nerve cells are killed.

Further, when the sieve electrodes of FIG. 3 as described above are inserted, a cross-talk between each electrode is generated. Thus, there is a problem that the electric signals are not correctly detected.

The present invention is proposed to solve problems of the prior arts, and one object of the present invention is to propose a neural device obtaining electric signals without killing nerve fibers.

Another object of the present invention is to propose a neural device that may elaborately obtain electric signals and transmit stimuli to nerve cells.

Technical Solution

To achieve the objects as described above, the neural device according to the present invention is characterized in that it comprises at least one nanowire inserted in a nerve to obtain electric signals from nerve fibers included in the nerve or to transmit stimuli thereto; and a processing module electrically connected with the nanowire.

In addition, the neural device according to the present invention is characterized in that it comprises at least one nanowire inserted in a nerve to obtain electric signals from nerve fibers included in the nerve; at lease one nanowire inserted in the nerve to transmit electric stimuli thereto; and a processing module electrically connected with each nanowire.

Preferably, the present invention is characterized in that it further comprises a base, connected to the processing module, providing with at least through-hole and nanowire support, wherein the nanowire support is formed by dividing the through-hole in multiple areas or being extended from the inner circumference of the through-hole, and wherein one end of the nanowire is fixed on the nanowire support.

In addition, a method of treating electric signals about nerve fibers according to the present invention comprises steps of incising some of a nerve; and inserting the neural device as described above in the incised portion.

Advantageous Effects

The neural device according to the present invention has an advantage that may obtain electric signals without killing nerve fibers or provide them with electric stimuli.

In addition, when the neural device according to the present invention is used, it has an advantage that may elaborately obtain electric signals and transmit stimuli to nerve cells.

BEST MODE

Specific features and effects of the present invention will be more embodied by examples of the present invention as explained below. The present examples are explained as follows, with reference to the attached drawings.

The neural device (or the nervous device) according to the present example includes nano-sized materials. The nano-sized materials have small size and increased aspect ratio. Thus, electrochemical reactions developed on their surfaces are so preferential that they may be used as various sensors. Especially, one-dimensional nano materials such as nano tubes, nano lines and nano bars have high aspect ratio to be easily handled, and thus have been primarily embodied as nano devices.

In the present example, the neural device based on nanowires is proposed, to obtain electric signals from a nerve. The neural device according to the present example is characterized by comprising at least nanowire obtaining electric signals from a nerve or transmitting electric stimuli thereto.

Figure 4:
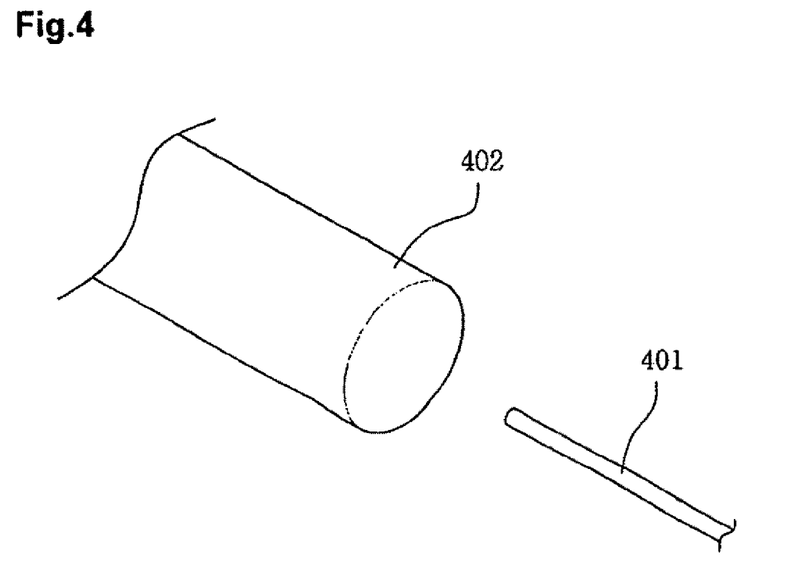
FIGS. 4 and 5 represents a nanowire included in the neural device according to the present example.

FIG. 4 represents a nanowire included in the neural device according to the present example.

The nanowire (401) according to the present example is characterized by obtaining electric signals from nerve fibers (402) or transmitting electric stimuli to the nerve fibers (402). A nerve, anatomically, is a fine long structure, and histologically, one that a number of nerve bundles are collected. Meanwhile, the nerve bundle is one that a number of nerve fibers are collected. The nerve fiber denotes a portion of axon in a nerve cell and is called as a term of nerve fiber, since the axon has a fine long shape as a fiber. The nerve fiber is called as various terms such as axon.

All the nerve fibers are each surrounded by endoneurium, soft connective tissue, the nerve bundles are surrounded by perineurium, and the nerve, a bundle of nerve bundles, is surrounded by epineurium. All these membranes are present for protecting the nerve, and only the epineurium is distinguished with naked eye.

As shown therein, the nanowire (401) according to the present example is inserted in the nerve fiber (402) to obtain electric signals or to provide it with electric stimuli. That is, the nanowire (401) according to the present example is inserted within a nerve fiber in a nerve bundle to obtain electric signals developing along with surface of the nerve fiber, or to provide the nerve fiber with stimuli.

Conventionally, electrodes prepared in a size of macro unit were arranged and inserted to nerve fibers. In this case, damage was caused in the nerve fiber that the electrodes were inserted and thus there was a problem that the nerve fibers were killed. However, in case of the present example, the nanowire (401) is used to obtain electric signals and/or provide them with electric stimuli, so that the damage to nerve fibers can be minimized.

The nanowire (401) has merely a diameter of scores to hundreds nm, and thus may be inserted in any portion of the nerve fiber (402). Generally, since the diameter of nerve fiber (402) is more than several micrometers, the nerve fiber (402) is not damaged, though the nanowire (401) is inserted.

Figure 5:
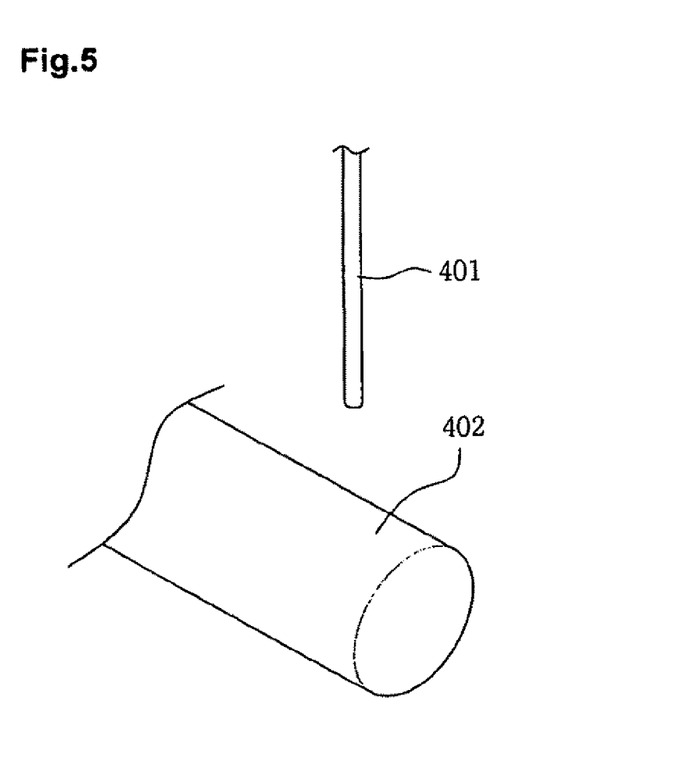

As shown in FIG. 4, the nanowire (401) is preferably inserted in the longitudinal direction. When the nanowire (401) is inserted in the longitudinal direction, the contact area between the nanowire (401) and the outer portion of nerve fiber (402) is easily maximized. Therefore, it is preferred to be inserted in the longitudinal direction. However, the direction of inserting the nanowire (401) is not limited. As shown in FIG. 5, the nanowire (401) may be also inserted in the direction perpendicular to the nerve fiber (402).

Figure 6:
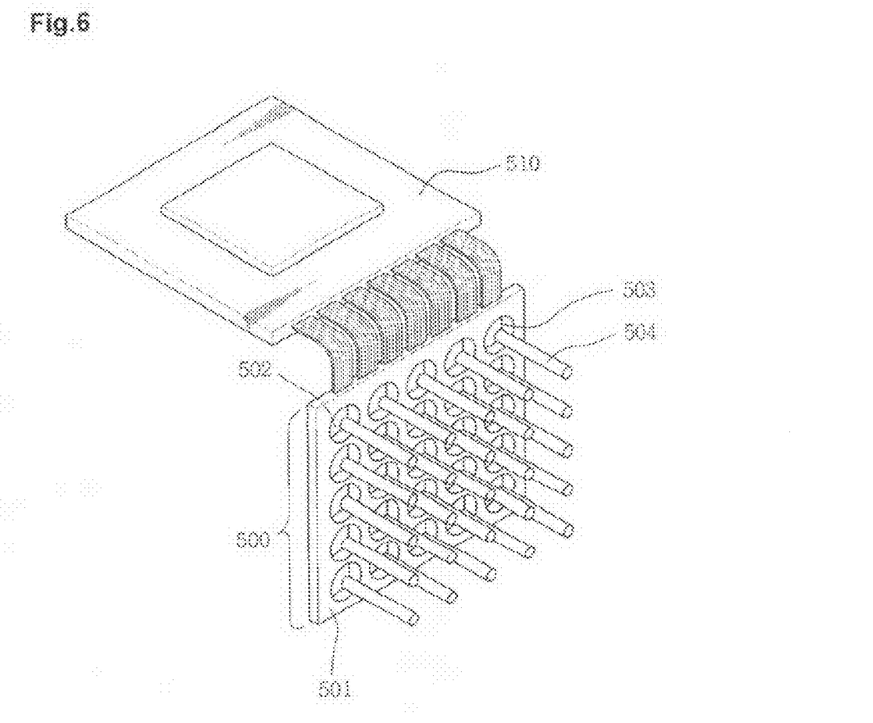
FIG. 6 represents a device comprising the neural device proposed in the present example.

FIG. 6 represents a device comprising nanowires proposed in the present example.

In the drawings mentioned below, each member is depicted by magnifying or reducing its size for convenience of explanation. Therefore, the present invention is not limited to specific values of the attached drawings.

The neural device according to the present example comprises electrodes and a processing module.

The electrodes (500) according to the present example are connected to the processing module (510) to process electric signals detected from the nerve fiber. The processing module (510) controls an operation to obtain electric signals from nerve fibers or to transmit electric signals to nerve fibers. The processing module (510) is a device which may be prepared by using conventional devices used in the prior arts as described above, and the like.

The electrodes (500) according to the present example provide the processing module (510) with the electric signals obtained from the nerve fibers, and transmit the electric stimuli to the nerve fibers according to control of the processing module (510).

The electrodes (500) according to one aspect of FIG. 6 include a base (501), through-holes (502), nanowire supports (503) and nanowires (504).

The base (501) is manufactured in a plate shape or various cubic shapes, and connected to the processing module (510). In the base (501), at least one through-hole (502) is preferably formed. The through-hole (502) may have various cross-sections such as a circle, an oval and a polygon, but is preferably manufactured in a shape of a circle to be easily formed or a shape corresponding to the cross-section of nerve bundle. Preferably, the through-hole has a diameter of several nm to scores nm.

In the inner circumference of the through-hole (502), nanowire support (503) is preferably provided. The nanowire support (503) holds the nanowire (504) to be fixed in one direction. Preferably, the nanowire (504) is fixed by the nanowire support (503).

FIG. 6 represents one embodiment that the electrodes (500) according to the present example are connected to one side of the processing module (510). The electrodes (500) to be connected to one side of the processing module (510) may obtain electric signals from the nerve fibers, transmit electric stimuli thereto, or simultaneously obtain electric signals and transmit electric stimuli. On one hand, the number of electrodes (500) to be connected to the processing module (510) is not limited. For example, two electrodes (500) may be connected to both sides opposite the processing module (510). In this case, it is preferred that the first electrode(s) connected to one side of the processing module (510) obtains electric signals from the nerve fibers and the second electrode(s) connected to the other side of the processing module (510) transmits electric stimuli to the nerve fibers.

The electrode (500) of FIG. 6 as described above may be manufactured by various methods. A method of growing into nanowire (504) and a method of preparing an electrode (500) providing with the nanowire (504), are explained as follows.

Figure 7:
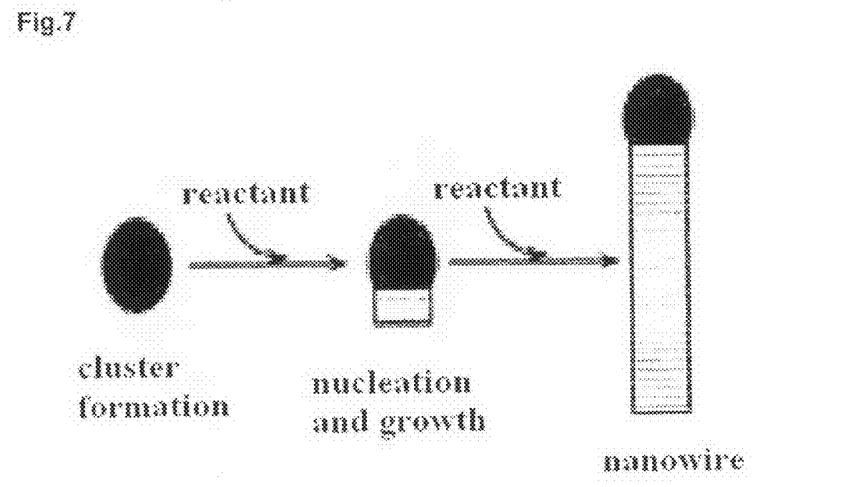
FIGS. 7 to 9 explain one aspect of a process for preparing the present invention.
Figure 8:
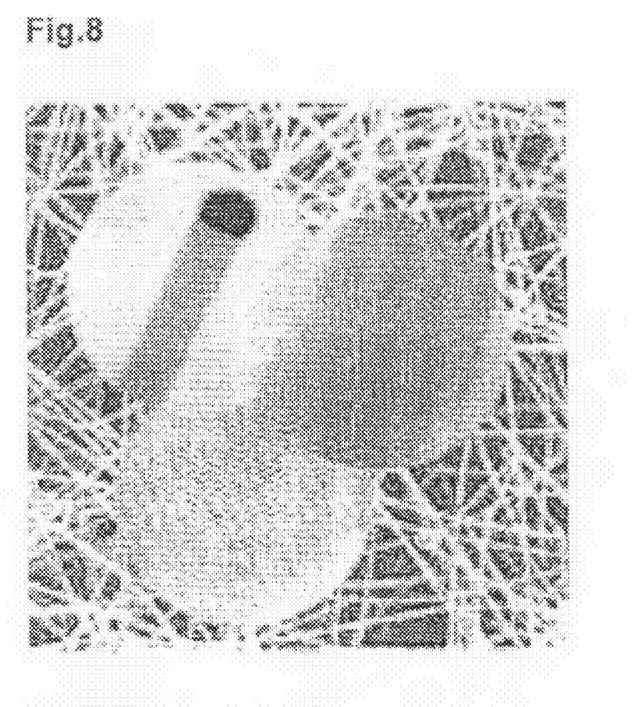

FIG. 7 is a schematic diagram explaining a method of synthesizing a nanowire using a catalyst. As shown therein, when the reactant is added to nano cluster, a nanowire is synthesized via nucleation and growth. The synthesized nanowire may have a shape as shown in FIG. 8. In addition, the nanowire used in the present example may be formed by any method described in a prior art (Si Nanowire Bridges in Trenches: Integration of Growth into Device Fabrication" Adv. Mater. 17, 2098, 2005).

Figure 9:
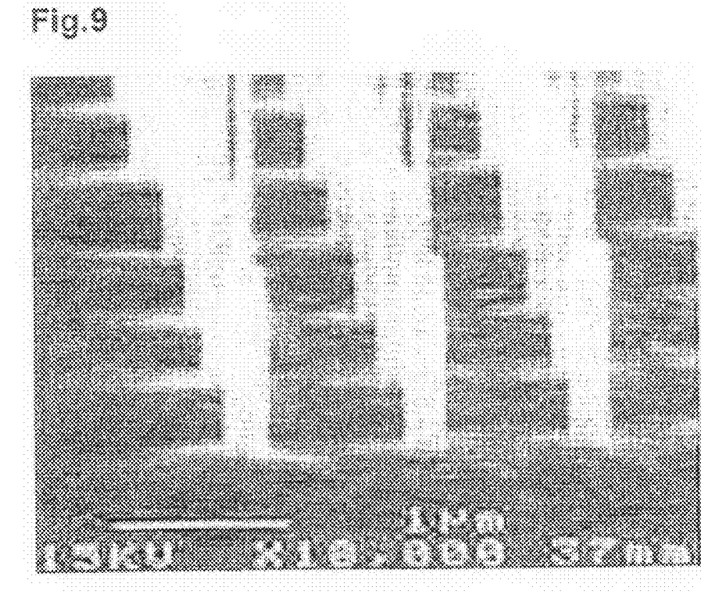

According to the described context, the nanowire having 3-dimensional structure, as shown in FIG. 9, may be manufactured.

One aspect of a method of preparing the electrode (500) including the nanowire as described above is explained below. The base (501) comprising the through-holes (502) and the nanowire supports (503) as described above may be implemented by applying a photomask process on a wafer of various materials such as silicon and an etching process.

When the base (501) including through-holes (502) and nanowire supports (503) is formed, a catalyst is positioned at a site that the nanowire (504) is growing on the nanowire support (503). For example, in case of fixing a nanowire (504) at the middle portion in the nanowire support (503), the catalyst for growing into nanowire (504) is positioned at the middle portion in the nanowire support (503). The catalyst may be positioned at any portion in the nanowire support (503) via a lithography process and the like. Preferably, the catalyst is selected depending on materials of nanowire (504) to be grown. For example, in case of growing into a silicon nanowire, an Au catalyst may be used. When the catalyst is positioned on a substrate, the reactants may be supplied via a CVD process and the like to finish the nanowire (504).

The base (501), nanowire supports (503) and nanowires (504) may be of various materials. For example, semiconductor materials or metals such as silicon, gold, silver and copper are available, which may be implemented into nano devices via nano processes.

Figure 10:
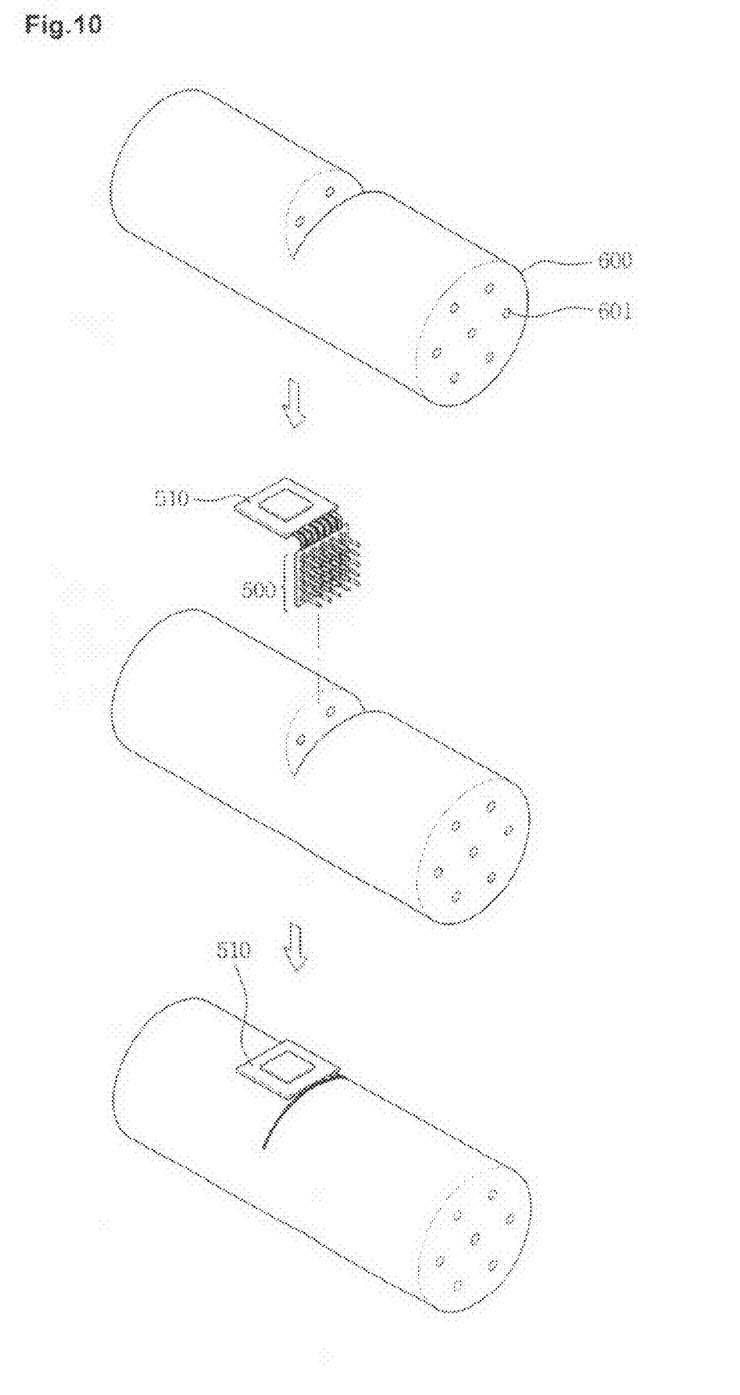
FIG. 10 represents one aspect that the electrode proposed in the present example is inserted.

FIG. 10 represents one aspect that the neural device proposed in the present example is inserted into a nerve. As shown above, the neural device according to the present example is inserted into a nerve. In order to insert the neural device into a nerve, the nerve is incised and the electrodes (500) are inserted in the incised gap.

Specifically, as shown in FIG. 10, the nerve (600) comprising nerve bundles (601) including a number of nerve fibers (not depicted) is incised and the electrodes (500) are inserted in the incised portion.

The direction, in which the electrodes (500) are inserted, is not limited, but preferably, the electrodes (500) are inserted for the nanowire included in the electrodes (500) to be inserted into a longitudinal direction in the nerve.

After inserting the electrodes (500), the incised nerve (600) is sutured.

When the incised nerve (600) is hold in a state of incision, there is a problem that the nerve is killed. However, since the incised nerve (600) is sutured after inserting the electrodes (500), the nerve anastomosis may be ingenerately restored. Particularly, the electrodes (500) according to the present example, as shown in FIG. 6, provide with at least one through-hole (502), and thus the incised nerve fibers are ingenerately restored via the through-holes (502). Therefore, there is an advantage that the electric signals developed in the nerve fibers are continuously obtained.

Figure 11:
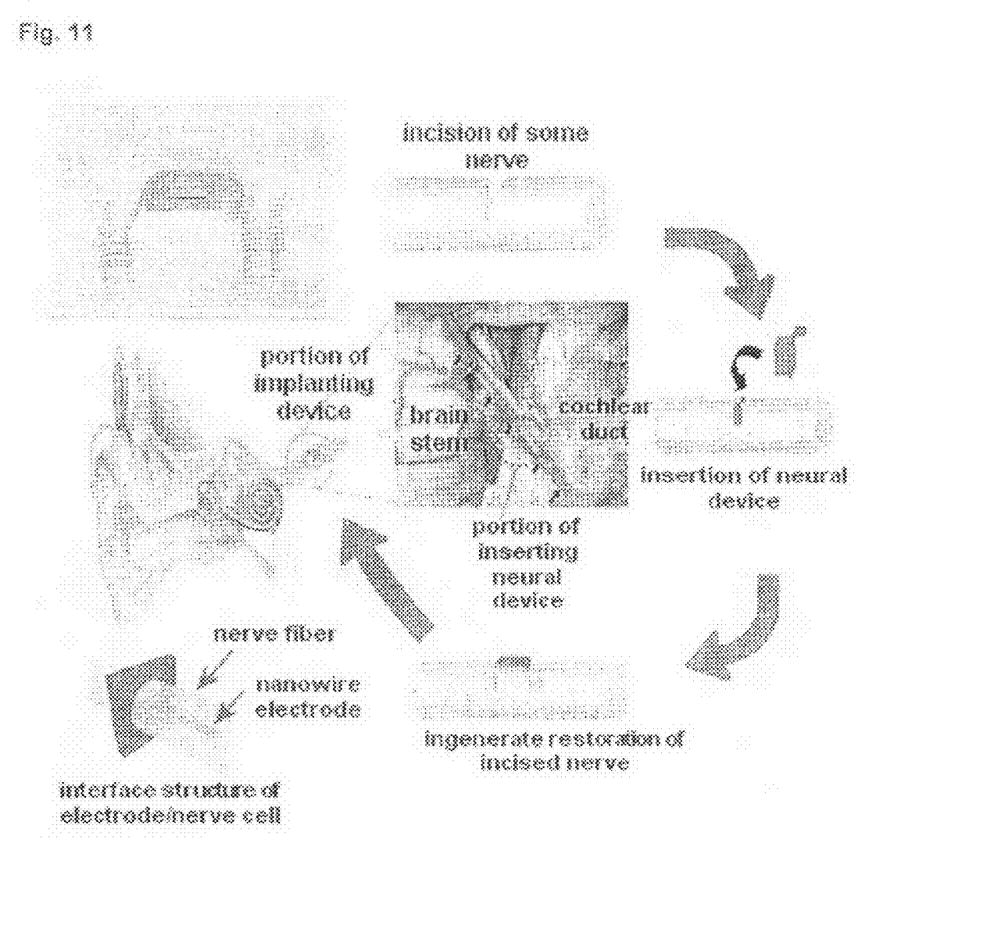
FIG. 11 represents one aspect inserting the neural device according to the present example.

FIG. 11 represents one aspect that the neural device according to the present example is inserted. As shown therein, after incising a portion of nerve and inserting the device, the electric signals in the nerve may be obtained, and the inserted nerve may be an auditory nerve.

Figure 12:
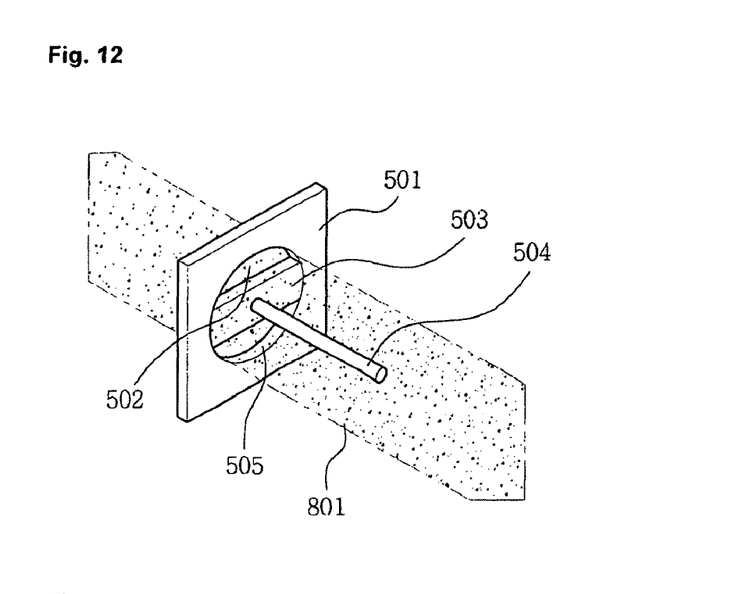
FIG. 12 represents a nerve restored via a through-hole.

FIG. 12 represents a nerve fiber restored via a through-hole.

As shown therein, the temporarily incised nerve fiber (801) is restored via the through-hole (502), and consequently the nanowire (504) in the nerve fiber (801) is inserted in a longitudinal direction of nerve. As shown in one aspect of FIG. 12, the base (501) is provided with through-holes (502), nanowire supports (503) are fixed on the inner circumferences (505) of through-holes (502), and nanowires (504) are fixed into the nanowire supports (503).

It is preferred that since the multi nerve fibers (801) are present in the same direction, the multi nanowires (504) are present in a certain direction. In addition, it is preferred that the nanowires (504) are disposed based on the predetermined array pattern, so that the nanowires (504) may be correctly inserted in the nerve fibers (801). For example, the nanowires (504) may be disposed in the same intervals, or densely disposed about the specific area. The nanowires (504) may be provided in a size of 100 by 100. That is, the nanowires may be disposed with an array of 100*100.

When multi nanowires (504) of FIG. 12 are provided, the nanowires (504) may be inserted in various portions of nerve fiber (801) (for example, the outside portion of nerve fiber).

Figure 13:
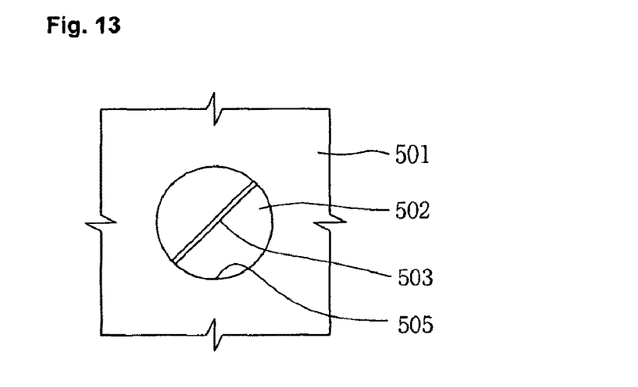
FIGS. 13 and 14 represent one aspect of shape that the nanowire support (503) is fixed on the through-hole (502).
Figure 14:
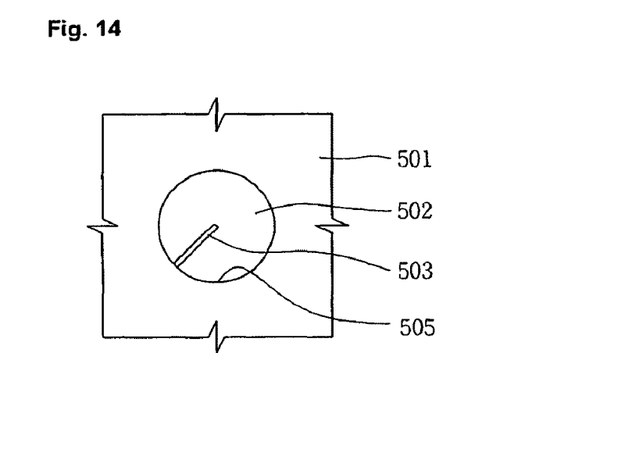

FIGS. 13 and 14 represent one aspect of shapes that the nanowire supports (503) are fixed on the through-holes (502). As shown in FIG. 13, the nanowire support (503) may be formed to divide the through-hole (502) into multi areas. The nanowire support (503) may have a straight line shape, as shown therein, or be formed in a curve having various curvatures. In addition, as shown therein, it may be extended from the inner circumference (505) of through-hole (502) or any one side of the base (501) to be formed.

On one hand, as shown in FIG. 14, one end of the nanowire support (503) may be fixed on the inner circumference (505) of through-hole (502), and the other end may be randomly positioned.

Mode for Invention

It is apparent to one skilled in this field that the present invention may be embodied into other specific aspects within the range not deviating from the spirit and essential features of the present invention. Therefore, the detailed description as above must not be restrictively interpreted in all sides and should be regarded as being illustrative. The scope of the present invention should be determined by reasonable interpretation in the attached claims and all modification within the range equivalent to the present invention is included in the scope of the present invention.

INDUSTRIAL APPLICABILITY

The electrodes according to the present invention may be used in various electric devices which obtain electric signals from nerve fibers and provide them with electric stimuli. Thus, the present invention is appropriately recognized as being industrially applicable.

The invention claimed is:

1. A neural device for at least one of obtaining electric signals from nerve fibers or transmitting signals thereto, comprising:
   at least one nanowire configured to be inserted in the nerve fibers;
   a processing module electrically connected with the at least one nanowire; and
   a base, connected to the processing module, the base comprising:
   a through-hole in the base comprising an inner circumference, and
   a nanowire support fixed to the inner circumference of the through-hole;
   wherein the at least one nanowire is attached to the nanowire support.

2. The neural device according to claim 1, further comprising a plurality of nanowires disposed in an array of 100*100.

3. The neural device according to claim 1,
   wherein each material of the base, nanowire and nanowire support is any one selected from silicon, gold, silver or copper.

4. The neural device according to claim 1, wherein the nanowire support is configured to divide the through-hole into multi areas.

5. A neural device to obtain electric signals from nerve fibers and to transmit stimuli thereto, comprising:
   at least one first nanowire configured to be inserted in nerve fibers to obtain electric signals from the nerve fibers;
   at least one second nanowire configured to be inserted in the nerve fibers to transmit electric stimuli thereto;
   a processing module electrically connected with the at least one first and second nanowires; and
   a base, connected to the processing module, the base comprising:
   first and second through-holes in the base comprising first and second inner circumferences, and
   first and second nanowire supports fixed to the first and second inner circumferences, respectively;
   wherein the at least one first and second nanowires are attached to the first and second nanowire supports, respectively.

6. The neural device according to claim 5,
   wherein each material of the base, nanowire and nanowire support is any one selected from silicon, gold, silver or copper.

7. The neural device according to claim 5, wherein the first and second nanowire supports are configured to divide the first and second through-holes into multi areas, respectively.

* * * * *